(12) United States Patent
Stritzke et al.

(10) Patent No.: US 9,063,095 B2
(45) Date of Patent: Jun. 23, 2015

(54) TEST METHOD AND TEST APPARATUS FOR TESTING ELONGATED OBJECTS USING COIL

(75) Inventors: Günther Stritzke, Gomaringen (DE); Stefan Koch, Bisingen (DE)

(73) Assignee: Institut Dr. Foerster GmbH & Co. KG (DE)

( * ) Notice: Subject to any disclaimer, the term of this patent is extended or adjusted under 35 U.S.C. 154(b) by 1094 days.

(21) Appl. No.: 13/125,391

(22) PCT Filed: Oct. 22, 2009

(86) PCT No.: PCT/EP2009/007564
§ 371 (c)(1),
(2), (4) Date: Jun. 7, 2011

(87) PCT Pub. No.: WO2010/046106
PCT Pub. Date: Apr. 29, 2010

(65) Prior Publication Data
US 2011/0234213 A1    Sep. 29, 2011

(30) Foreign Application Priority Data

Oct. 23, 2008 (DE) .......................... 10 2008 053 778

(51) Int. Cl.
*G01N 27/82* (2006.01)
*G01N 27/90* (2006.01)

(52) U.S. Cl.
CPC ................................. *G01N 27/9026* (2013.01)

(58) Field of Classification Search
CPC ................................................ G01N 27/9026
USPC ............................................................ 324/238
See application file for complete search history.

(56) References Cited

U.S. PATENT DOCUMENTS

| 3,361,960 | A | 1/1968 | Renken, Jr. et al. |
| 3,872,379 | A | 3/1975 | Brooks et al. |
| 4,954,777 | A | 9/1990 | Klopfer et al. |
| 5,184,070 | A | 2/1993 | Besendorfer et al. |
| 6,344,740 | B1 * | 2/2002 | Haberlein ..................... 324/226 |

FOREIGN PATENT DOCUMENTS

| DE | 29 05 399 A1 | 8/1979 |
| DE | 40 03 330 A1 | 8/1991 |
| DE | 44 38 171 A1 | 5/1996 |
| DE | 44 43 464 C2 | 7/1998 |

(Continued)

OTHER PUBLICATIONS

DE4443464 Machine Translation by EPO, p. 1-16, patent of record.*

(Continued)

*Primary Examiner* — Thomas F Valone
(74) *Attorney, Agent, or Firm* — DLA Piper LLP (US)

(57) ABSTRACT

A test method for testing elongated objects comprising moving an elongated object in a feed-through direction through a feed-through coil arrangement having at least one feed-through coil, wherein the feed-through coil arrangement is secured to be transversely movable with respect to the feed-through direction of the object and is guided on the object passing through such that the feed-through coil arrangement can follow transverse movements of the object occurring transversely with respect to the feed-through direction of the object.

26 Claims, 5 Drawing Sheets

(56) References Cited

FOREIGN PATENT DOCUMENTS

| | | |
|---|---|---|
| DE | 1 319 955 A1 | 6/2003 |
| EP | 0 231 865 A2 | 8/1987 |
| GB | 1 484 696 | 9/1977 |
| GB | 2 014 317 A | 8/1979 |
| JP | 52-37989 | 3/1977 |
| JP | 61-146763 | 9/1986 |
| JP | 01-203965 | 8/1989 |
| JP | 03-68054 | 7/1991 |

OTHER PUBLICATIONS

Bae, Hot wire inspection using eddy current, Tech Res Lab, p. 1-5, no date.*
Mizuno, JP 03-068054, Jul. 3, 1991, p. 1-17, PTO Translation.*
Takano, JP 61-146763, Sep. 10, 1986, p. 1-17, PTO Translation.*
Yoshida, JP 52-037989, Mar. 17, 1977 p. 1-7, PTO translation.*
Japanese Official Action dated Apr. 1, 2014 along with an English translation from corresponding Japanese Application No. 2011-532536.

* cited by examiner

TEST METHOD AND TEST APPARATUS FOR TESTING ELONGATED OBJECTS USING COIL

RELATED APPLICATIONS

This is a §371 of International Application No. PCT/EP2009/007564, with an international filing date of Oct. 22, 2009 (WO 2010/046106 A1, published Apr. 29, 2010), which is based on German Patent Application No. 10 2008 053 778.0, filed Oct. 23, 2008, the subject matter of which is incorporated by reference.

TECHNICAL FIELD

This disclosure relates to a test method for testing elongated objects, in which an elongated object is moved through in a feed-through direction through a feed-through coil arrangement having at least one feed-through coil, and to a test apparatus for testing elongated objects using a feed-through method with a feed-through coil arrangement having at least one feed-through coil for feeding through an elongated object in a feed-through direction.

BACKGROUND

Elongated objects such as, for example, metallic wires, bars, rods or tubes can serve as starting materials for high quality end products and are frequently subject to extremely high quality requirements. Testing for material flaws, for example, for cracks near to the surface, cavities or other material inhomogeneities, forms an important part of the quality control of these products. In this context, as far as possible uninterrupted testing of the material surface with a high resolution is generally aimed at, which testing is to be carried out where possible at the manufacturing location in synchronism and at the speed of the manufacturing process. Nowadays such tests are often carried out using magnetic methods, in particular eddy current technology in a feed-through method. When testing using a feed-through method, an object which is to be tested (test specimen) is moved at a relatively high feed-through speed through a test section equipped with the corresponding sensor system, and the object is tested in the process.

One class of test apparatuses for the feed-through method has a test head which rotates about the object passing through and has test probes which are mounted thereon and which, given suitable matching of the rotational speed and the feed-through speed permit uninterrupted testing of the objects with a high spatial resolution. In another class of feed-through methods, feed-through coils, which surround the test specimen and through which the object to be tested is guided, are used.

During the non-destructive testing of materials using the eddy current method, an exciter coil is used to generate an electrical alternating current (eddy current) with a suitable direction, magnitude and frequency in the material to be tested, and the irregularities which are produced in the eddy current are detected and evaluated using sensors, for example, a coil arrangement. In eddy current testing, use is made of the effect according to which most impurities or defects in an electrically conductive material have a different electrical conductivity and/or different permeability from that of the test material itself. The measurement signal to be evaluated is determined in particular from the conductivity and permeability of the material of the test specimen and from the distance between the eddy current sensor and the surface of the material, wherein the absolute strength of the fault signal and also the ratio between the useful signal and interference signals (signal-to-noise ratio) decrease as the distance of the sensor from the surface of the material increases.

To compensate for the strong influence of the distance between the sensor and the surface of the material on the measurement signal, various systems for distance compensation have been proposed for test apparatus with rotating heads (such as, for example, DE 40 03 330 A1). The influence of the distance of the test coils, arranged at a distance from the item to be tested, corresponds to the so-called "fill factor" of the feed-through coil in the methods which use feed-through coils. What is referred to as the fill factor is generally understood to be the ratio of the cross section of the test material to the effective coil cross section. It is generally observed that the fault signal amplitude decreases the smaller the fill factor. For this reason, attempts are made to fill the cross section of the feed-through coil as far as possible by the test specimen, with the result that the inner regions of the feed-through coils extend relatively close to the surface to be tested. However, particularly in tests with a relatively high fill factor of the feed-through coil, relatively high interference levels which adversely affect the measuring accuracy are frequently observed. It has been observed that this effect can occur particularly in relatively thin test materials such as, for example, wires or thin bars.

It could therefore be helpful to provide a test method for testing elongated objects using feed-through coils, which test method permits testing with a high flaw signal level and at the same time a low interference level, in particular even in relatively thin test specimens such as wires or thin bars. It could also be helpful to provide a test apparatus which is suitable for carrying out the method.

SUMMARY

We provide a test method for testing elongated objects including moving an elongated object in a feed-through direction through a feed-through coil arrangement having at least one feed-through coil, wherein the feed-through coil arrangement is secured to be transversely movable with respect to the feed-through direction of the object and is guided on the object passing through such that the feed-through coil arrangement can follow transverse movements of the object occurring transversely with respect to the feed-through direction of the object.

We also provide a test apparatus for testing elongated objects using a feed-through method with a feed-through coil arrangement with at least one feed-through coil for feeding through an elongated object in a feed-through direction including a securing device that secures the feed-through coil arrangement in a test position, wherein the securing device permits movements of the feed-through coil arrangement transversely with respect to the feed-through direction, and by a guide device for adjusting the location of the test position of the feed-through coil arrangement as a function of the location of the object passing through the feed-through coil arrangement.

BRIEF DESCRIPTION OF THE DRAWINGS

FIG. 7 shows, in 7A, an oblique perspective view of a feed-through coil arrangement in which guide rollers for rolling on a guided-through object are attached on the inflow side and the outflow side, as well as an optionally attachable spring bracket, and in 7B an axial view of a guide roller which rolls on the test specimen.

DETAILED DESCRIPTION

The test method of the type mentioned above is defined by the fact that the feed-through coil arrangement is secured to be transversely movable with respect to the feed-through direction of the object and is guided on the object passing through such that the feed-through coil arrangement can follow transverse movements of the object occurring transversely with respect to the feed-through direction of the object. As a result, it becomes possible that even when transverse movements of an object passing through occur the feed-through coil always remains arranged symmetrically around the object. Therefore, continuous self-centering of the feed-through coil or of the feed-through coil arrangement occurs at the object passing through, with the result that during the test the radial distance from the facing inner side of the feed-through coil does not change at any location on the circumference of the object passing through. As a result, the interference level or the signal-to-noise ratio can be kept very low independently of the fill factor of the feed-through coil because the interference influences due to fluctuations in distance are largely eliminated by the structurally provided self-centering of the feed-through coil arrangement at the object passing through.

A test apparatus suitable for carrying out the method and for testing elongated objects using a feed-through method with a feed-through coil arrangement with at least one feed-through coil for feeding through an elongated object in a feed-through direction has a securing device for securing the feed-through coil arrangement in a test position, wherein the securing device permits movements of the feed-through coil arrangement transversely with respect to the feed-through direction, and a guide device for adjusting the location of the test position of the feed-through coil arrangement as a function of the location of the object passing through the feed-through coil arrangement. In this context, the test position of the feed-through coil of the feed-through coil arrangement is advantageously such that the feed-through coil is centered with respect to the cross section of the object passing through. In the case of a test specimen with a circular cross section, it is possible to use, for example, a feed-through coil which has a round cross section and whose central coil axis is always essentially coaxial to the central longitudinal axis of the object passing through, irrespective of transverse movements of the object passing through.

Feed-through coils can also be used for other, non-circular cross sections, for example, for a rectangular cross section, a triangular cross section, an elliptical or oval cross section or an egg-shaped cross section. The cross sections of the feed-through coils should then have a correspondingly matched cross-sectional shape.

In many method alternatives, the feed-through coil arrangement is guided directly on the object passing through. In this context, continuous contact can occur between the object passing through and one or more guide elements of the guide device, which guide elements are assigned to the feed-through coil arrangement and can move therewith. The contact may be, for example, a sliding contact or a rolling contact. A combination of sliding and rolling is also possible.

In many instances, the feed-through coil arrangement has at least one guide sleeve for guiding through the object to be tested, wherein an effective internal cross section of the guide sleeve is configured for essentially play-free sliding on the test specimen. The feed-through coil can enclose the guide sleeve and can be arranged between the axial ends of the guide sleeve, for example, approximately centrally between the ends. A central axis of the guide sleeve can be arranged coaxially with respect to the coil axis of the feed-through coil, with the result that when the object passing through is centered in the guide sleeve the object passing through is also centered with respect to the feed-through coil.

Alternatively or additionally it is also possible for the feed-through coil arrangement to be connected to at least one roller arrangement which has at least one guide roller for rolling on the object which is moved through the feed-through coil arrangement. This permits particularly gentle guidance contact with the object. The roller arrangement preferably has at least one guide roller before the feed-through coil arrangement in the feed-through direction and at least one guide roller after the feed-through coil arrangement in the feed-through direction, with the result that the feed-through coil arrangement is arranged between guide rollers of the roller arrangement. This permits reliable centering with minimum loading of the object to be tested. A guide roller can have a concave guide contour on its circumference, with the result that the guide roller can center itself on the object passing through, which also permanently ensures the centering of the feed-through coil with respect to the test specimen passing through. If the concave guide contour is essentially in a V shape, the same guide roller can be used for test specimens with different diameters, wherein centering takes place in all cases over a certain diameter range.

Contactless guidance of the feed-through coil arrangement at the object passing through is also possible and may be provided, for example, if objects with particularly contact-sensitive surfaces are to be tested. In one method alternative, a current position of the object passing through is detected before the feed-through coil arrangement in the feed-through direction, i.e., at the entry side of the feed-through coil arrangement, using a position sensor for generating position signals, and a displacement drive or centering drive for displacing the feed-through coil arrangement transversely with respect to the feed-through direction of the object is controlled on the basis of the position signals in such a way that the feed-through coil is displaced dynamically using the displacement drive, i.e., in near to real-time conditions for the detection of possible transverse movements of the object, into such a test position in which the object passing through extends essentially centrally through the feed-through coil arrangement. For example, optical or magnetic position sensors can be used for the detection of the axial position of the object.

The securing device for securing the feed-through coil arrangement is intended to secure the feed-through coil arrangement in a test position, and at the same time permit limited movement of the feed-through coil arrangement transversely with respect to the feed-through direction of the object. This is possible in different ways. In many instances, the securing device has a coil holder for attaching the feed-through coil arrangement and a base element for attachment to a component which is permanently connected to the machine base of the test apparatus, wherein the coil holder is connected to the base element via a movable connecting device in such a way that the coil holder can move, with respect to the base element, in at least two spatial directions extending transversely with respect to the feed-through direction. As a result, the feed-through coil arrangement can follow possible transverse movements of the object to be tested, but it remains essentially secured in the feed-through direction.

In one alternative, the connecting device comprises at least two pivot joints with pivoting axes which are oriented perpendicularly with respect to one another, with the result that a relative movement of the coil holder with respect to the base element is possible in at least two spatial directions extending perpendicularly with respect to one another.

In some examples, two pairs of pivot joints with pivoting axes which are respectively oriented perpendicularly with respect to one another are provided. If the feed-through coil arrangement has more than two degrees of freedom of movement for pivoting movements compared to the machine base, the feed-through coil can follow not only the object passing through which are in transverse movements but orientation of the feed-through coil arrangement with the object is also possible, as a result of which measurement errors due to tilting are minimized and states of the feed-through coil arrangement which lead to the production of tilting torques or of other nonuniform loads are counteracted.

It is also possible for the connecting device to have at least one flexible connecting element which connects the coil holder to the base element. In one example, the base element is connected via a connecting wire to the coil holder which can therefore move with respect to the base element, without being able to follow the test specimen in the feed-through direction.

Floating bearing of the coil holder with respect to the base element is possible as a further alternative, which bearing can have, for example, two or more linear guides which are oriented perpendicularly with respect to one another.

It is also possible to use an elastically resilient spring arrangement, which connects the coil holder to the base element. The spring arrangement can have one or more springs such that the coil holder is held in a reference position which corresponds to an ideal feed-through and that certain deflections with respect to this reference position due to the elasticity of the spring arrangement are possible. The connecting device can be formed by the spring arrangement or can contain such an arrangement in addition to other components, for example, a connecting wire.

Ferromagnetic test materials, for example, steel tubes, steel wires or steel bars frequently exhibit variations in permeability which do not constitute flaw which are looked for but which can perceptibly disrupt the testing or even make it impossible since they can generate large interference signals. These interference signals can be reduced by magnetic saturation of the test material at the location of the feed-through coil. For this purpose, in many examples, a magnetization device which can move with the feed-through coil arrangement or is arranged in a positionally, fixed fashion with respect to the feed-through coil arrangement is provided for magnetizing the object passing through the feed-through coil arrangement. The magnetization device preferably has magnetization means before a feed-through coil in the feed-through direction and after a feed-through coil in the feed-through direction, of the feed-through coil arrangement, the magnetization means being in particular in the form of permanent magnets whose dimensioning should be adapted to the cross section of the object to be tested. The magnetization means can be configured in such a way that they generate magnetic flux lines in the material of the test specimen, which flux lines extend, in the region of the feed-through coil, essentially parallel to the longitudinal direction of the object passing through. Instead of permanent magnets, coils which are fed with direct current, and which generate a magnetic direct current field essentially parallel with respect to the longitudinal axis of the material, can also be used instead of permanent magnets. This permits magnetization with a magnetization field strength which can vary over time.

If the material of the object to be tested has been magnetized for the test, the material of the test specimen generally remains at least partially magnetized after the test section of the test apparatus has been passed through. Since this is generally undesirable, in many examples, a demagnetization device which is arranged after the feed-through coil arrangement in the feed-through direction is provided. The demagnetization device may be provided spatially and structurally separate from the feed-through coil arrangement, but preferably it moves along with the feed-through coil arrangement which follows the test specimen. This can be achieved, for example, by virtue of the fact that the securing device for securing the feed-through coil arrangement also has securing structures for holding a demagnetization device. The securing structures can, for example, be configured in such a way that when necessary the demagnetization device can be easily attached to the securing device or released therefrom when no demagnetization is required.

These features and further features can be found both in the claims and in the description and the drawings, wherein the individual features are respectively implemented per se or as a plurality in the form of secondary combinations in one example, and can be implemented in other fields and can constitute advantageous examples for which protection can be sought. Examples are illustrated in the drawings and will be explained in more detail below.

Figure 1:
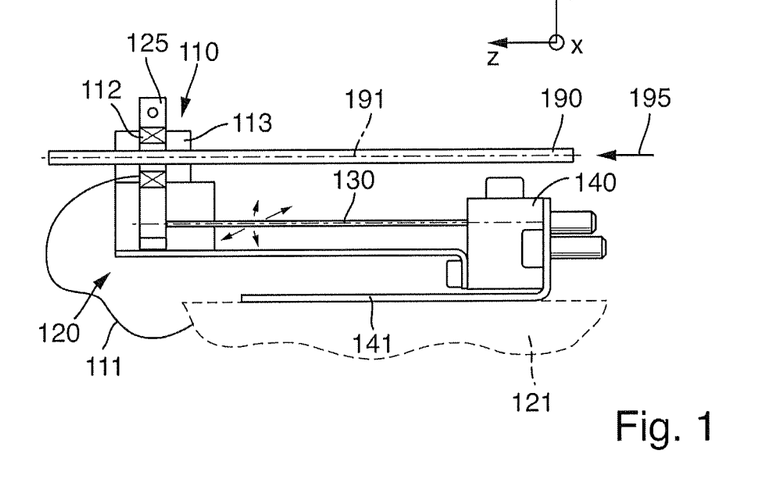
FIG. 1 shows a schematic side view of essential components of a first example of a test apparatus in which a coil holder for a feed-through coil arrangement is connected in a movable fashion via a flexible connecting wire to a base element which is attached to the machine base of the test apparatus.
Figure 2:
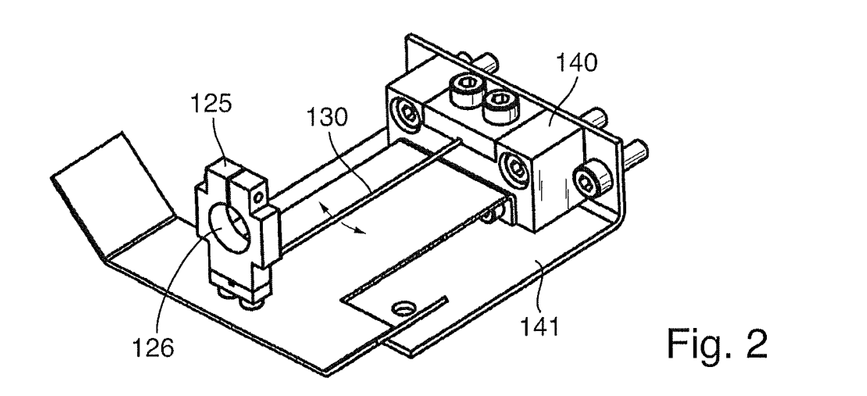
FIG. 2 shows a perspective plan view of the example in FIG. 1.

The partially sectional side view in FIG. 1 shows essential components of an example of a test apparatus for eddy current testing of elongated objects (test specimens) in a feed-through method by feed-through coils. The components of the test apparatus which are shown can be arranged directly after the outlet of a fabrication machine for elongated objects, for example, a wire drawing machine. The test specimen 190, which is, in the example, a metallic wire with a circular cross section and a diameter between approximately 0.3 mm and approximately 2-3 mm, has a central longitudinal axis 191 and moves parallel with respect to this longitudinal axis in an essentially horizontal movement direction (arrow) which runs from right to left in the drawing. For example, a winding-on device for the freshly drawn wire which is tested for faults directly after the drawing can be located downstream of the test apparatus, that is to say on the outlet side.

The test apparatus has a feed-through coil arrangement 110 with at least one schematically illustrated feed-through coil 112 through which the object to be tested is moved for the testing in a feed-through direction 195 which corresponds to the movement direction, wherein the feed-through coil surrounds the test specimen during the test. The surrounding feed-through coil 112 is connected in a manner known per se as a transmission coil and as a receiver coil of an eddy current measurement device. The feed-through coil can comprise, for example, two measuring coils which are connected in opposition to one another and are arranged at an axial distance from one another and can be electrically connected according to DE 44 43 464 C2.

The feed-through coil arrangement is attached using a securing device 120 to a component 121, mounted on the machine base, of the test apparatus. The component may be, for example, part of the control unit of the test apparatus which contains the electrical components for energizing the feed-through coil arrangement and for detecting signals and carrying out evaluation. The feed-through coil arrangement can be connected in a detachable fashion to the control unit via a flexible connecting cable 111 and plug-in contacts.

The feed-through coil arrangement has, in the example, an essentially cylindrical housing 113 into which the feed-through coil 112 and further components of the feed-through coil arrangement are permanently integrated. Some examples are explained in more detail below in FIGS. 3 to 5. The securing device 120 comprises a coil holder 125 with a cylindrical through-opening 126 which can be widened to a limited degree and into which the feed-through coil arrangement can be introduced axially to be subsequently secured in the coil holder by tightening clamping screws. The coil holder is connected to a base element 140 of the securing device via a single flexible connecting element in the form of a connecting wire 130, which base element 140 comprises a base plate 141 which can be attached to the upper side of the component 121 using screws.

If the feed-through direction 195 of the object to be tested is defined as the z direction and the x and y directions which are oriented perpendicularly with respect to the feed-through direction are defined as the transverse directions with respect to the feed-through direction, it is clear that with the flexible connection between the base element 140 and the coil holder 125 the coil holder and the feed-through coil arrangement held therein are capable of moving relative to the base element in all transverse directions, in particular both in the horizontal direction (x direction) and in the vertical direction (y direction), while a movement parallel with respect to the feed-through direction (z direction) is largely prohibited when the connecting wire is stretched.

The feed-through coil arrangement has a guide sleeve for guiding through the object to be tested, wherein the internal cross section of the guide sleeve is dimensioned in such a way that the guide sleeve can slide essentially free of play on the test subject guided through it. Details will be explained further below in conjunction with FIGS. 3 to 6. The guide device which is equipped with the guide sleeve causes the longitudinal axis 191 of the wire always to be located in a centered fashion in the feed-through coil, that is to say coaxially with respect to the central coil axis. During the operation of the test apparatus, the test subject matter 190 is guided through the feed-through coil arrangement with a suitable feed-through speed and in the process, it can carry out more or less pronounced transverse movements perpendicularly with respect to the feed-through direction 195 depending on the configuration of the elements provided on the input side and output side for guiding the test specimen and on the mechanical and elastic properties of the test specimen. These transverse movements can lead in conventional feed-through coil arrangements to considerable disruption of the measurement since the measurement signals of the feed-through coil arrangement depend greatly on the distance between the surface of the material of the test specimen and the inside of the through-coil. In the example shown, these faults are reduced or avoided by virtue of the fact that, thanks to the flexible suspension, the feed-through coil can follow the transverse movements of the test specimen with the result that the location of the feed-through coil is automatically adjusted as a function of the location of the object passing through the feed-through coil or the feed-through coil arrangement. Since the test specimen always extends through the feed-through coil arrangement in a centered fashion independently of its absolute position in the space, contributions by faults which are distant-dependent are largely suppressed, with the result that a measurement can be made with a very low distance-dependent interference level.

Figure 3:
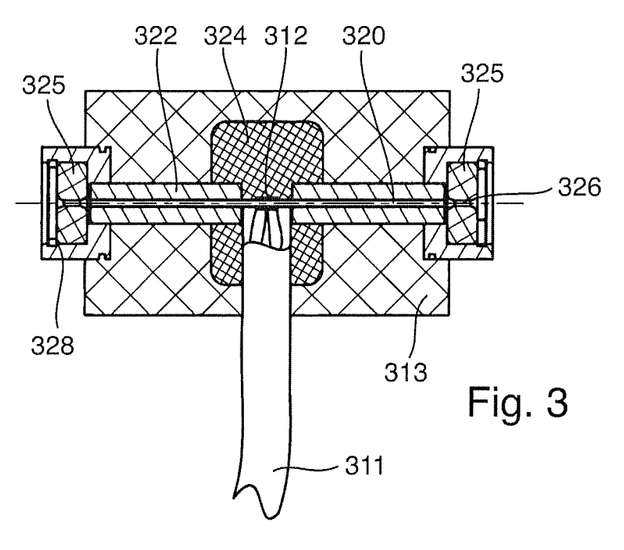
FIG. 3 shows a longitudinal section through a first example of a feed-through coil arrangement.

A number of examples of lightweight and compact feed-through coil arrangements, such as can be used, for example, in testing wires for wire cross sections between approximately 0.3 mm and 2 mm to 3 mm near to the point of fabrication, will now be given with respect to FIGS. 3 to 6. The feed-through coils of the feed-through coil arrangement in FIG. 3 are formed by two measuring coils 312 which are arranged at an axial distance from one another and can be connected to the control electronics of the test apparatus via a multi-conductor connecting cable 311 to form a difference coil pair. The measuring coils are seated approximately centrally on a thin-walled tube 320 which is composed of a nonmagnetic material, for example, of an austenitic steel, of glass, of ceramic, of plastic, of a suitable hard metal or of a composite material.

The thin-walled tube 320 has a plurality of functions. It serves, on the one hand, as a guide sleeve of the feed-through coil arrangement and has for this purpose an internal diameter which is only slightly larger than the external diameter of the metal wire to be guided therethrough. The fit is preferably to be selected such that it is possible for the test specimen to slide through the sleeve in a way which is essentially free of play on all sides. A possible air gap between the surface of the test specimen and the inside of the tube may be, for example, in the range up to a maximum of 30 μm to 50 μm or at maximum 60 μm or at maximum 80 μm and may be selected in accordance with the surface properties of the test specimen. The material of the guide sleeve should be selected with respect to large operating lives of the feed-through coil arrangement and also according to wear criteria, and should be, if possible, wear-resistant with respect to the material of the test specimen to be guided through. A further function is that the nonmagnetic material of the tube 320 ensures that a ferromagnetic object which is guided through does not stay adhered or "stuck magnetically" to magnetic or magnetized parts of the feed-through coil arrangement. The tube therefore forms a magnetic insulator between the test specimen and the test apparatus.

To permit measurement with a large fill factor despite the magnetic separation, the wall thickness of the tube should be very small. The thickness may be, for example, less than 0.25 mm and, in particular, in the range from 0.1 mm to 0.2 mm.

Depending on the wall thickness of the tube 320, very large fill factors, for example, of more than 70%, can be achieved during the testing. In particular, the fill factor can be in the range between approximately 75% and approximately 95%. For example, fill factors between approximately 70% and approximately 80% can be achieved relatively easily.

Relatively strong supporting tubes 322 made of a magnetically conductive material, for example, a suitable steel material, can be fitted onto the guide sleeve 320 on both sides of the measuring coil in such a way that only a small air gap remains between the end faces of the supporting tubes facing the measuring coils and the measuring coils. To secure these elements to one another and to protect the sensitive measuring coil, the connecting cable which leads to the measuring coils and the ends of the supporting tubes 322 which face the measuring coils, these elements are enclosed with a resin sheath 324 and as a result stabilized mechanically and at the same time protected against damage. This structural unit composed of elements which are secured to one another forms the basic unit of the feed-through coil arrangement and is already fully functionally capable.

To improve the function further, guide nozzles 325 which can be replaced are provided at both ends of the guide sleeve 320, the internally polished nozzle openings 326 of which guide nozzles 325 are arranged coaxially with respect to the central axis of the guide sleeve. The guide nozzles are held replaceably in aluminum holders 328 which are fitted onto the respective ends of the steel tubes 322. The guide nozzles are widened conically at their respective outer sides to facilitate feeding in of the test specimen. The nozzle element can be composed, for example, of a diamond material or plastic.

The overall arrangement is encased with a cast resin mixture which, after curing, forms an air-tight and liquid-tight, essentially cylindrical housing 313 of the feed-through coil arrangement, from which housing 313 only the nozzle holders with the replaceable guide nozzles introduced therein project on both sides and the connecting cable 311 projects radially. The easy-to-mount, extremely compact and lightweight feed-through coil arrangement has excellent protection against mechanical, thermal and chemical influences from the outside and can therefore be used near to the point of fabrication, for example, directly after the outlet of a drawing die of a drawn wire device over long times without significant worsening of functions.

Figure 4:
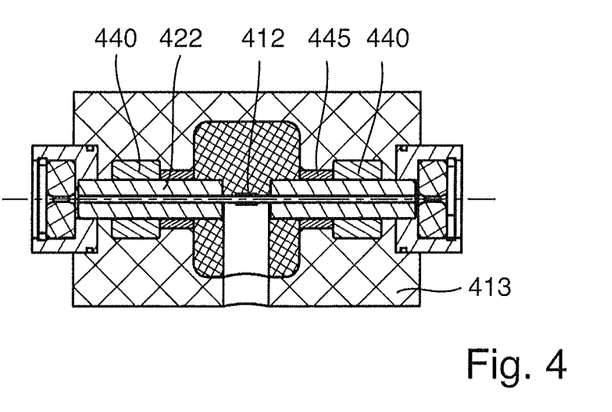
FIG. 4 shows a longitudinal section through a second example of a feed-through coil arrangement.
Figure 5:
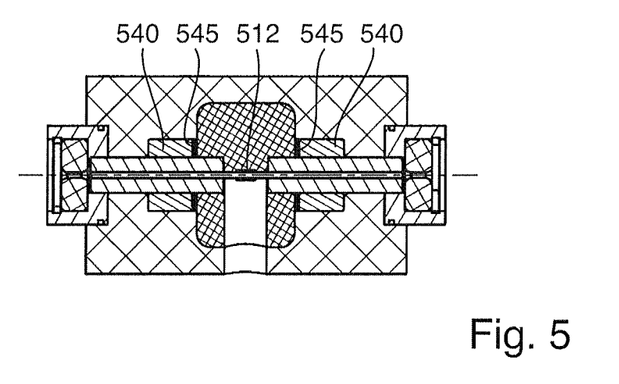
FIG. 5 shows a longitudinal section through a third example of a feed-through coil arrangement.
Figure 6:
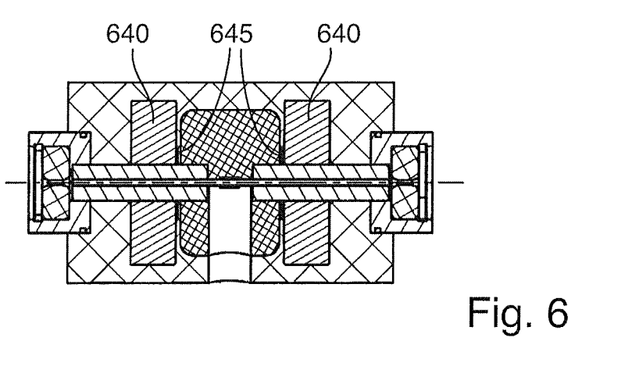
FIG. 6 shows a longitudinal section through a fourth example of a feed-through coil. arrangement.

While FIG. 3 shows an example without a magnetization device for magnetizing the test specimen passing through, FIGS. 4 to 6 show various examples with such a magnetization device. These alternatives can provide advantages, in particular, if ferromagnetic test materials are to be checked with which, owing to variations in permeability in the test material, it can be different or even impossible to separate the flaw signals originating from the flaws which are being looked for from the interference signals which are caused by variations in permeability. The magnetization means serve in this case to magnetically homogenize the test material and to reduce the variations in permeability in the region of the feed-through coils, as a result of which the signal-to-noise ratio can be improved. In the examples in FIGS. 4 to 6, those components which are present in identical or corresponding form in the simpler example according to FIG. 3 are provided with corresponding reference symbols, increased by 100 or integral multiples thereof.

The magnetization device comprises two permanent magnets 440 which are arranged symmetrically with respect to the measuring coils 412 and which have the same orientation of the magnetic poles to generate, in the region of the measuring coil, a magnetic field with magnetic flux lines running essentially parallel to the longitudinal direction of the guide tube. The correct orientation of the permanent magnets can be easily determined during mounting as a result of the fact that the permanent magnets which are fitted onto the tubes have to attract one another. The axial distance between the permanent magnets 440 and the measuring coils is adjusted using tubular spacer elements 440 which are fitted onto the supporting tubes 422 before the permanent magnets are fitted on from the ends. After the spacers and the permanent magnets have been fitted on, the holders for the guide nozzles are fitted on at the ends in a way already described before the entire assembly is cast with casting resin to form the housing 413. The magnetically conductive supporting tubes 422 serve also as magnetic flux conductors here.

If a relatively strong magnetization magnetic field is to be present when there are identically dimensioned permanent magnets at the location of the measuring coil, the permanent magnets can be moved closer to the measuring coil. FIG. 5 shows in this respect an example in which, instead of the tubular spacers, only narrow shim rings 545 are interposed, with the result that the axial distance between the permanent magnets and the measuring coils is less than in the example according to FIG. 4.

A further variation of the magnetic field strength at the location of the measuring coil is possible, for example, by virtue of the fact that instead of the relatively small permanent magnets of the examples in FIGS. 4 and 5, relatively strong permanent magnets can be used. In this respect, FIG. 6 shows by way of example two permanent magnets 640 with a relatively large volume of the magnetic material, which permanent magnets 640 are moved close to the measuring coil with the interposition of spacers 645.

Figure 7A:
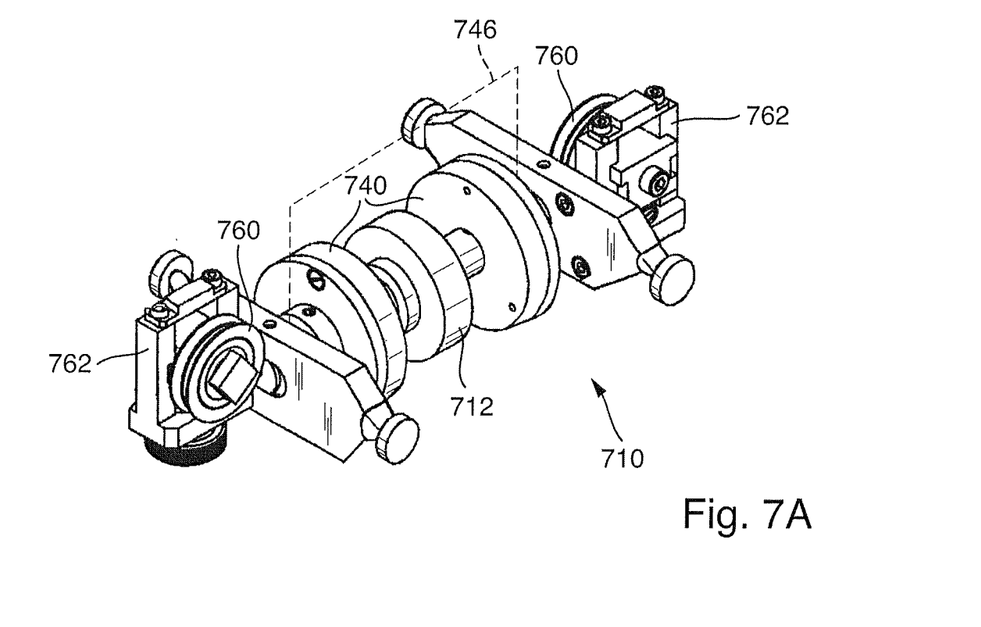
Figure 7B:
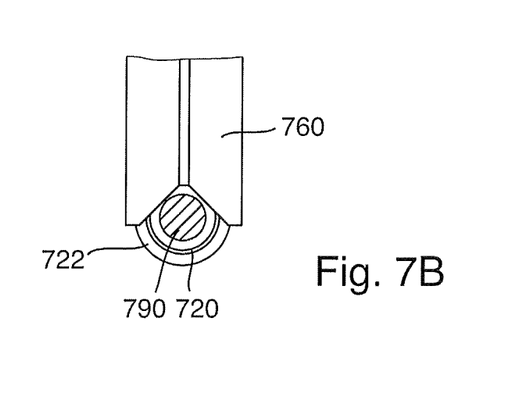

FIGS. 7A and 7B now explain an example which is configured in particular for testing somewhat thicker wires starting from approximately 2 to 3 mm in diameter or also for testing correspondingly dimensioned bars or tubes. It is possible to cover, for example, diameters up to the region of 15 mm to 20 mm. Generally, the components of the feed-through coil arrangement are generally larger and heavier the larger the diameter of the object to be tested. On the other hand, the objects to be tested are generally guided before and after the location of the test apparatus and given a sufficient material cross section between the guides they can bear a sufficient load to be able to support even relatively heavy feed-through coil arrangements. The feed-through coil arrangement 710 comprises an internal tube 720 which is shown in an axial view in FIG. 7B, is composed of a nonmagnetic material and has, in contrast to the guide sleeves of the previous examples, an internal diameter which can be significantly larger than the external diameter of the test specimen, with the result that contact between the test specimen and the inside of the tube during the test is avoided. Supporting tubes 722 made of magnetically conductive material are fitted onto the tube in a way analogous to the examples above. The measuring coils of the feed-through coils 712 are seated centrally on the inner tube 720. Two magnetization magnets 740 of a magnetization device are fitted onto the outer tubes 722 on both sides of the measuring coils at a distance therefrom, and are fixed in their axial positions by screws.

The feed-through coil arrangement has, similarly to the examples in FIGS. 3 to 6, a tube arrangement with an inner tube 720 and at least one outer tube 722 which surrounds the inner tube, wherein the inner tube 720 is composed essentially of a nonmagnetic material and the outer tube 722 is composed essentially of a magnetically conductive material, and can therefore serve as part of the magnetization means. The feed-through coil surrounds the inner tube in a region without an outer tube, and part of the outer tube is arranged on the two sides of the feed-through coil. While the inner tube in the examples in FIGS. 3 to 6 serves as a guide sleeve and slides on the tested object, in the alternative in FIG. 7 there is normally no provision of contact with the object and the guidance is ensured by a roller arrangement.

Roller carriers 762, which bear guide rollers 760 which are mounted on the respective roller carriers to be rotatable about rotational axes which are oriented perpendicularly with respect to the feed-through direction and are largely horizontal during operation, are fixed to both axial ends of the feed-through coil arrangement. The roller carriers are arranged on opposite sides of the longitudinal axis of the arrangement or of a test specimen guided therethrough, in an approximately rotationally symmetrical fashion with respect to the center of gravity of the overall arrangement, which is located in the region of the measuring coil, with the result that distribution which is balanced in terms of weight is obtained. The guide rollers 760 which are composed, at least in their circumferential region, of bronze or some other nonmagnetic and preferably wear-resistant material (for example, plastic, Vulkollan®, etc.) have on their circumference a concave, essentially V-shaped guide contour which ensures that the guide rollers on the test specimen guided therethrough center themselves in the lateral direction when the overall arrangement is suspended from the test specimen. FIG. 7B shows this situation in which a guide roller 760 is seated centrally on a test specimen 790 which is guided through in the feed-through direction (perpendicularly with respect to the plane of the paper). The guide rollers are dimensioned and arranged here such that the central axis of the test specimen then runs centrally through the inner tube 720 of the feed-through coil arrangement without making contact with the inner tube. All the components of the roller arrangement should, where possible, be fabricated from nonmagnetic materials to prevent the roller arrangement having an adverse effect on the magnetic field distribution in the region of the measuring coils.

In this example, a particularly effective magnetization of the test specimen can be achieved by virtue of the fact that the magnetization device comprises a magnetically conductive device 746 for closing magnetic field lines outside the feed-through coil arrangement. This device is configured in the example in FIG. 7A as a field bar 746 (illustrated only schematically by dashed lines) composed of magnetically conductive material. This field bar can be permanently securely connected to the feed-through coil arrangement, but in the example shown it is configured as a field bar which can be removed when necessary and which can be attached and removed from the feed-through coil arrangement without using tools.

Figure 8:
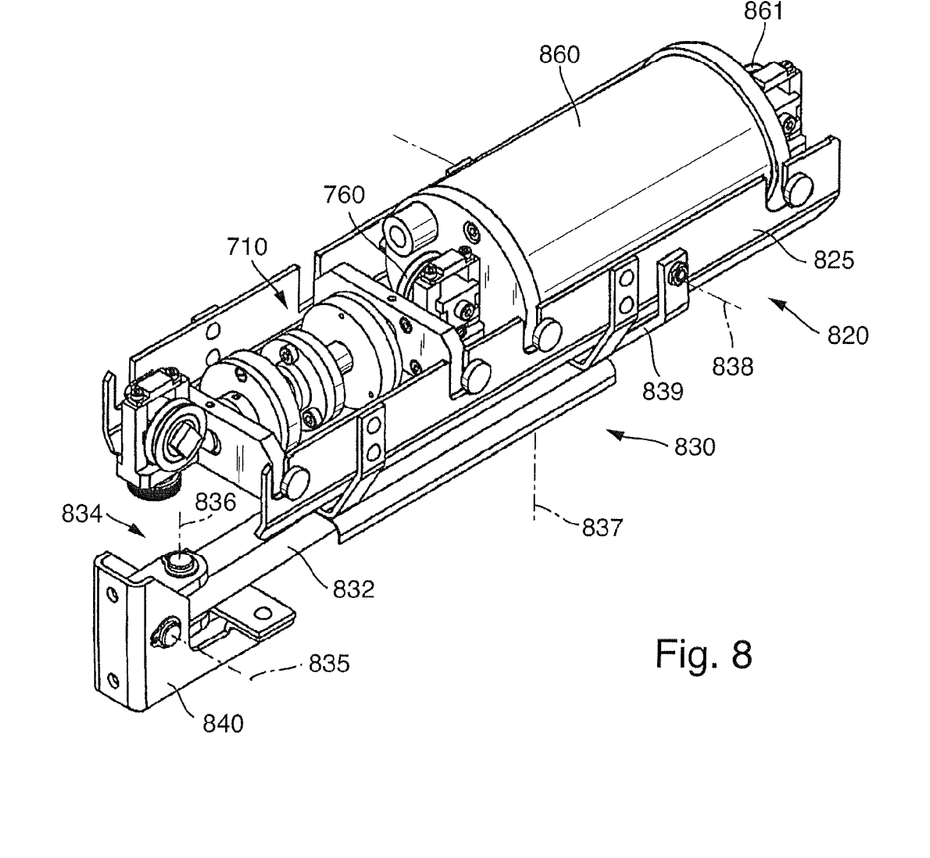
FIG. 8 shows an oblique perspective illustration of a securing device having a plurality of pivot bearings, which a feed-through coil arrangement with an integrated magnetization device for magnetizing ferromagnetic material to be tested is arranged in the securing device, and a demagnetization device which can move with the feed-through coil arrangement is arranged after the feed-through coil arrangement.

FIG. 8 shows the feed-through coil arrangement 710 which is shown in FIG. 7, in an operationally-ready mounted state in which the feed-through coil arrangement is inserted into a securing device 820 which during operation of the testing device permits the feed-through coil arrangement to follow possible transverse movements of the test specimen passing through, while maintaining the centering of the test specimen in the feed-through coil arrangement. The securing device comprises an upwardly opened coil holder 825 which is in the form of a ship and which has, on its upwardly projecting side walls, L-shaped indents from which the feed-through coil arrangement can be suspended using outwardly projecting pins. The securing device also has an essentially angular base element 840 which permits the securing device to be attached to part of the test apparatus fixed to the machine. In the example, through-going drilled holes for securing screws, with which the securing device can be screwed tight directly to the draw die holder of a draw die device, are provided on the vertical front side of the base element. Using the horizontal part of the angle, the base element can also be attached to the upper side of another component fixed to the machine.

The base element 840 and the coil holder 825 are connected by a connecting device 830 which can move per se. The connecting device 830 comprises a pivoting arm 832 which is connected to the base element 840 via a joint arrangement 834 with two pivoting axes which are oriented perpendicularly with respect to one another. A horizontal first pivoting axis 835 permits a pivoting movement of the pivoting arm in the vertical direction, while a vertical second pivoting axis 836 permits additional lateral pivoting. Arranged at the end of the pivoting arm facing the coil holder is a second joint arrangement which also comprises two pivoting axes which are oriented perpendicularly with respect to one another. An essentially U-shaped, upwardly opened securing bar 839 is connected via a pivoting joint to the pivoting arm in such a way that the pivoting axis 837 of this joint extends perpendicularly with respect to the longitudinal axis of the pivoting lever 832. The coil holder 825 is mounted pivotably between the arms of the securing bar, wherein the associated pivoting axis 838 extends perpendicularly with respect to the pivoting axis 837. The two joint arrangements make it possible for the coil holder which is connected to the base element to be moved both in the vertical direction and in the lateral direction, that is to say in all the transverse directions with respect to the feed-through direction, while maintaining an essentially horizontal orientation of the feed-through axis. This facilitates, on the one hand, the mounting of the arrangement and the feeding in of a test specimen. Furthermore, this allows the test arrangement to follow possible transverse movements of the test specimen passing through, while maintaining the centering of the test specimen in the feed-through coil arrangement. Moreover, the securing device also keeps the feed-through coil arrangement in the vicinity of the feed-through region if a test specimen tears off, for example, or the end of a long test specimen has passed through the feed-through coil arrangement. It therefore acts as a means for protecting against dropping out.

One particular feature of the example in FIG. 8 consists in the fact that a demagnetization device 860 in the form of a large permanent magnet or an electromagnet is arranged on the coil holder 825, behind the feed-through coil arrangement 710 in the feed-through direction. Outwardly projecting pins, which can be used to install the demagnetization device in the coil holder from above in a positively locking fashion, are also provided on the demagnetization device. The outlet-side guide roller 760 of the feed-through coil arrangement forms at the same time the inlet-side guide roller of the demagnetization device, at the outlet side of which a further guide roller 861 is located, to ensure central guidance of the tested test specimen and the still magnetizing test specimen by the demagnetization device.

The invention claimed is:

1. A test apparatus for testing elongated objects using a feed-through method with a feed-through coil arrangement with at least one feed-through coil for feeding through an elongated object in a feed-through direction comprising:
 a securing device that secures the feed-through coil arrangement in a test position, wherein the securing device permits movements of the feed-through coil arrangement transversely with respect to the feed-through direction, and by a guide device for adjusting the location of the test position of the feed-through coil arrangement as a function of the location of the object passing through the feed-through coil arrangement,
 wherein the securing device has a coil holder for attaching the feed-through coil arrangement and a base element for attachment to a component which is permanently connected to a machine base of the test apparatus, wherein the coil holder is connected to the base element via a movable connecting device such that the coil holder can move with respect to the base element in at least two spatial directions extending transversely with respect to the feed-through direction, and wherein the connecting device has two pairs of pivot joints with pivoting axes which are respectively oriented perpendicularly with respect to one another.

2. The test apparatus as claimed in claim 1, wherein the guide device has a roller arrangement which has at least one guide roller for rolling on the object which is moved through the feed-through coil arrangement.

3. The test apparatus as claimed in claim 2, wherein the roller arrangement has at least one guide roller before the feed-through coil arrangement in the feed-through direction and at least one guide roller after the feed-through coil arrangement in the feed-through direction such that the feed-through coil arrangement is arranged between guide rollers of the roller arrangement.

4. The test apparatus as claimed in claim 3, wherein a guide roller has, on its circumference, a concave guide structure which is configured essentially in a V shape and/or wherein a guide roller comprises a nonmagnetic material at least in the region of its circumference.

5. The test apparatus as claimed in claim 1, wherein a magnetization device, which can move with the feed-through coil arrangement, magnetizes the object passing through the feed-through coil arrangement.

6. The test apparatus as claimed in claim 5, wherein the magnetization device has a magnetizer with permanent magnets before a feed-through coil in the feed-through direction, and after a feed-through coil in the feed-through direction, of the feed-through coil arrangement.

7. The test apparatus as claimed in claim 1, wherein the feed-through coil arrangement has a tube arrangement with an inner tube and an outer tube surrounding at least a portion of the inner tube, wherein the inner tube is composed essentially of a nonmagnetic material, and the outer tube is composed essentially of a magnetically conductive material, wherein the feed-through coil encloses the inner tube in a region without an outer tube, and part of the outer tube is arranged on both sides of the feed-through coil.

8. The test apparatus as claimed in claim 5, wherein the magnetization device comprises a magnetically conductive device that closes magnetic field lines outside the feed-through coil arrangement.

9. The test apparatus as claimed in claim 1, comprising a demagnetization device arranged after the feed-through coil arrangement in the feed-through direction and can be fixed or is fixed relative to the feed-through coil arrangement such that said demagnetization device moves along with the feed-through coil arrangement following the test specimen.

10. The test apparatus as claimed in claim 1, wherein the securing device that secures the feed-through coil arrangement has securing structures for holding a demagnetization device.

11. A test apparatus for testing elongated objects using a feed-through method with a feed-through coil arrangement with at least one feed-through coil for feeding through an elongated object in a feed-through direction comprising:
a securing device that secures the feed-through coil arrangement in a test position, wherein the securing device permits movements of the feed-through coil arrangement transversely with respect to the feed-through direction, and by a guide device for adjusting the location of the test position of the feed-through coil arrangement as a function of the location of the object passing through the feed-through coil arrangement,
wherein the securing device has a coil holder for attaching the feed-through coil arrangement and a base element for attachment to a component which is permanently connected to a machine base of the test apparatus,
wherein the coil holder is connected to the base element via a movable connecting device such that the coil holder can move with respect to the base element in at least two spatial directions extending transversely with respect to the feed-through direction, and
wherein the connecting device has at least one flexible connecting element which connects the coil holder to the base element, wherein the base element is connected to the coil holder via a connecting wire.

12. The test apparatus as claimed in claim 11, wherein a magnetization device, which can move with the feed-through coil arrangement, magnetizes the object passing through the feed-through coil arrangement.

13. The test apparatus as claimed in claim 12, wherein the magnetization device has a magnetizer with permanent magnets before a feed-through coil in the feed-through direction, and after a feed-through coil in the feed-through direction, of the feed-through coil arrangement.

14. The test apparatus as claimed in claim 11, wherein the feed-through coil arrangement has a tube arrangement with an inner tube and an outer tube surrounding at least a portion of the inner tube, wherein the inner tube is composed essentially of a nonmagnetic material, and the outer tube is composed essentially of a magnetically conductive material, wherein the feed-through coil encloses the inner tube in a region without an outer tube, and part of the outer tube is arranged on both sides of the feed-through coil.

15. The test apparatus as claimed in claim 12, wherein the magnetization device comprises a magnetically conductive device that closes magnetic field lines outside the feed-through coil arrangement.

16. The test apparatus as claimed in claim 11, comprising a demagnetization device arranged after the feed-through coil arrangement in the feed-through direction and can be fixed or is fixed relative to the feed-through coil arrangement such that said demagnetization device moves along with the feed-through coil arrangement following the test specimen.

17. The test apparatus as claimed in claim 11, wherein the securing device that secures the feed-through coil arrangement has securing structures for holding a demagnetization device.

18. A test apparatus for testing elongated objects using a feed-through method with a feed-through coil arrangement with at least one feed-through coil for feeding through an elongated object in a feed-through direction comprising:
a securing device that secures the feed-through coil arrangement in a test position, wherein the securing device permits movements of the feed-through coil arrangement transversely with respect to the feed-through direction, and by a guide device for adjusting the location of the test position of the feed-through coil arrangement as a function of the location of the object passing through the feed-through coil arrangement,
wherein the guide device has at least one guide sleeve for guiding through the object to be tested, wherein an effective internal cross section of the guide sleeve is configured for essentially play-free sliding on the test specimen, wherein an air gap between the surface of the object and an inner face of the guide sleeve is at maximum 50 µm and the feed-through coil encloses the guide sleeve.

19. The test apparatus as claimed in claim 18, wherein the guide sleeve has a wall thickness of less than 0.25 mm.

20. The test apparatus as claimed in claim 18, wherein the guide sleeve comprises at least one of a nonmagnetic material selected from the group consisting of a nonmagnetic steel material, a ceramic, glass, plastic and a composite material.

21. The test apparatus as claimed in claim 18, wherein a magnetization device, which can move with the feed-through coil arrangement, magnetizes the object passing through the feed-through coil arrangement.

22. The test apparatus as claimed in claim 21, wherein the magnetization device has a magnetizer with permanent magnets before a feed-through coil in the feed-through direction, and after a feed-through coil in the feed-through direction, of the feed-through coil arrangement.

23. The test apparatus as claimed in claim 18, wherein the feed-through coil arrangement has a tube arrangement with an inner tube and an outer tube surrounding at least a portion of the inner tube, wherein the inner tube is composed essentially of a nonmagnetic material, and the outer tube is composed essentially of a magnetically conductive material, wherein the feed-through coil encloses the inner tube in a region without an outer tube, and part of the outer tube is arranged on both sides of the feed-through coil.

24. The test apparatus as claimed in claim 21, wherein the magnetization device comprises a magnetically conductive device that closes magnetic field lines outside the feed-through coil arrangement.

25. The test apparatus as claimed in claim 18, comprising a demagnetization device arranged after the feed-through coil arrangement in the feed-through direction and can be fixed or is fixed relative to the feed-through coil arrangement such that said demagnetization device moves along with the feed-through coil arrangement following the test specimen.

26. The test apparatus as claimed in claim 18, wherein the securing device that secures the feed-through coil arrangement has securing structures for holding a demagnetization device.

* * * * *